US00PP13188P2

(12) United States Plant Patent
Utecht

(10) Patent No.: US PP13,188 P2
(45) Date of Patent: Nov. 5, 2002

(54) GERANIUM PLANT NAMED 'FISTANEON'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/989,368

(22) Filed: Nov. 21, 2001

(65) Prior Publication Data

US 2002/0083503 P1 Jun. 27, 2002

(51) Int. Cl.[7] ..... A01H 5/00

(52) U.S. Cl. ..... Plt./329

(58) Field of Search ..... Plt./329

*Primary Examiner*—Kent L. Bell
(74) *Attorney, Agent, or Firm*—Foley & Lardner

(57) ABSTRACT

A new and distinct cultivar of geranium plant named 'Fistaneon', as described and illustrated, and particularly characterized by the combined features of brilliant red-purple, semi-double flowers with scarlet markings, dark-green foliage with weak zonation, moderately vigorous growth and medium to tall plant habit.

1 Drawing Sheet

BOTANICAL CLASSIFICATION

*Pelargonium zonale.*

VARIETY DENOMINATION

'Fistaneon'.

BACKGROUND OF THE INVENTION

The present invention comprises a new and distinct cultivar of geranium, botanically known as *Pelargonium zonale,* and hereinafter referred to by the cultivar name 'Fistaneon'.

'Fistaneon' is a product of a planned breeding program which had the objective of creating new geranium varieties with purple colored, semi-double flowers in combination with dark-green foliage.

'Fistaneon' originated from a hybridization made by the inventor Angelika Utecht in a controlled breeding program in Galdar, Gran Canaria, Spain, in 1995. The female parent was an unpatented hybrid seedling, no. K93-998-11, having dark-pink, semi-double flowers, medium green, zoned foliage, and medium sized plant habit. The male parent of 'Fistaneon' was an unpatented hybrid seedling, no. K92-876-2, which was characterized by purple-pink, single-type flowers, dark-green foliage with zonation, relatively well-branched, round plant habit, but late flowering.

'Fistaneon' was selected as one flowering plant within the progeny of the state cross by Angelika Utecht in 1996 in a controlled environment in Galdar, Gran Canaria, Spain. The first act of asexual reproduction of 'Fistaneon' was accomplished when vegetative cuttings were taken from the initial selection in the fall of 1996 in a controlled environment in Galdar, Gran Canaria, Spain, by, or under the supervision of, Angelika Utecht.

Horticultural examination of plants grown from cuttings of the plant initiated in May 1998, in Hillscheid, Federal Republic of Germany, and continuing thereafter, has demonstrated that the combination of characteristics as herein disclosed for 'Fistaneon' are firmly fixed and are retained through successive generations of asexual reproduction. The new cultivar reproduces true to type.

'Fistaneon' has not been observed under all possible environmental conditions. The phenotype may vary significantly with variations in environment such as temperature, light intensity and day length. The following observations, measurements, and comparisons describe plants grown in Hillscheid, Germany, and in Langley, British Columbia, Canada, under greenhouse conditions which approximate those generally used in commercial practice.

BRIEF DESCRIPTION OF THE INVENTION

The following traits have been repeatedly observed and are determined to be basic characteristics of 'Fistaneon' in combination distinguish this geranium as a new and distinct cultivar:

1. Brilliant red-purple flowers with scarlet eyes on upper petals;

2. Medium to large sized, semi-spherically shaped umbels;

3. Dark-green foliage with weak zonation;

4. Moderately vigorous growth, and medium to tall plant habit; and

5. Medium to late spring flowering response.

Of the many commercial cultivars known to the present inventor, the most similar in comparison to 'Fistaneon' is the variety 'Fistangoli' (U.S. Plant Pat. No. 12,274), and the variety 'Fisrovio' (U.S. Plant patent application Ser. No. 09/991,663). In comparison to 'Fistangoli', 'Fistaneon' has a somewhat more reddish general flower color, not quite as big umbels as 'Fistangoli', but more vigorous growth and taller plant habit. In comparison to 'Fisrovio', 'Fistaneon' has a somewhat more intense flower color, darker green foliage, smaller leaves and plant habit is somewhat less tall.

BRIEF DESCRIPTION OF THE DRAWING

The accompanying photographic drawing shows typical flower and foliage characteristics of 'Fistaneon' with colors being as true as possible with an illustration of this type. The drawing shows a flowering pot plant in a 14 cm container.

DETAILED BOTANICAL DESCRIPTION

In the following description color references are made to The Royal Horticultural Society Colour Chart (R.H.S.). The color values were determined indoors from plants developed in a green-house in May 2001, in Hillscheid, Germany. The measurements were taken in Langley, British Columbia, Canada in early July, 2001, 18 weeks after planting of rooted cuttings. The plants were growing in 8 inch containers and had not been pinched.

INFLORESCENCE

Type: Umbel.
Shape: Semi-spherical.
Average diameter: 114 mm.
Average depth: 65 mm.
*Peduncle length*.—22.4 mm.
*Peduncle color*.—Green, RHS 143 A to RHS 143 B, weak infusion of brownish color may occur in parts, the resulting color is variable from RHS 146 A to RHS 176 D.
*Pedicel length*.—32.4 mm.
*Pedicel color*.—Reddish, from RHS 179 B, lower end, to RHS 181 A, upper end.
*Number of flowers per umbel*.—About 25 to 35.
Corolla:
*Average diameter*.—47 mm.
*Form*.—Semi-double.
*Shape*.—Round, slightly cup-shaped.
*Number of petals*.—8.7.
*Number of petaloids*.—0–1.
*Shape of petals*.—Obovate, base attenuate, upper end is rounded, margin is entire.
*Size of petals*.—Upper petals 25–27 mm long, 17–19 mm wide lower petals 20–22 mm long, 20–22 mm wide.
*Color* (*general tonality from a distance of three meters*).—Deep bluish red with scarlet markings.
*Color of upper petals*.—Main part RHS 57 A to RHS 57 B.
*Markings of upper petals*.—Lower part, about half the length of the petal, scarlet, RHS 44 A, and dark red veins, RHS 53 B, weak.
*Color of lower petals*.—RHS 66 B.
*Markings of lower petals*.—None.
*Color of lower surface of petals*.—Upper petals mainly RHS 47 A, lower petals RHS 66 B.
*Petaloid shape*.—Irregular.
*Petaloid color*.—Upper surface is RHS 57 B, Lower surface is RHS 66 B.
*Color of sepals*.—Outer surface mainly dark-red, RHS 184 A, tips are green, RHS 137 D; inner surface brownish-red, RHS 179 A, tips green, RHS 137 D.
*Number of sepals*.—5.
*Shape of sepals*.—Linear to lanceolate, acute tip, truncate base, surface with moderate pubescence, margin entire.
*Size of sepals*.—10–11 mm long, 4 mm wide for the largest upper sepal, 2–3 mm in width for the other sepals.
Bud: (just before petals unfold):
*Shape*.—Elliptical.
*Color* (*sepals*).—Mainly brown, RHS 184 A, tips RHS 137 D.
*Color* (*petals*).—RHS 66 B.
*Length*.—21 mm.
*Width*.—13 mm.
Reproductive organs:
*Androecium*.—7 fertile anthers, white to light pink filaments, RHS 155 D to RHS 66 D, plenty of pollen, yellow-orange, RHS 30 A.
*Gynoecium*.—One pistil, dark-red style and stigma, RHS 53 A, 5 to 6 lobed stigma.
*Fertility/seed set*.—Moderate seed set, mainly in late summer to fall. Fruit: Oblong, about 6 mm wide, rostrum (beak) 38–42 mm long. Seed: Oblong, 4–5 mm long, brown, RHS 177 B.
Spring flowering response period: In Hillscheid, Germany, in 2000 plants had on average 0.6 flowers opened 9 weeks after planting of rooted cuttings.
Outdoor flower production: Continuously flowering, the flower count in 2000 in Hillscheid, Germany, indicated about 2.9 inflorescence per plant in mid May.
Durability: Good stability of flower color, relatively good rain resistance.
Lastingness of the individual flower: About 8–9 days at 18° C., about 18–20 days for the umbel.
Pest/disease resistance/susceptibility: No observations made.
Fragrance: None.

PLANT

Foliage:
*Shape*.—Kidney-shaped to nearly round, with cordate, open base, weak lobes.
*Margin*.—Bicrenated, slightly wavy.
*Texture*.—Upper surface smooth, velvety.
*Size of leaf*.—86.5 mm wide, 57 mm long.
*Color of upper surface*.—Dark-green, approximately RHS 137 A.
*Color of zonation*.—Dark-green, RHS 139 A.
*Color of lower surface*.—RHS 137 D.
*Petioles*.—45–55 mm long, diameter 3 mm, medium green in color, approximately RHS 137 C.
General appearance and form:
*Stem color*.—Green, from RHS 137 D to RHS 143 A.
*Internode length*.—10–20 mm.
*Branching pattern*.—6.4 branches.
*Size of plants*.—Height 27.6 cm, as measured from the top of the soil (or base of the main stem) to the surface of the foliage canopy (measured without inflorescence); width 43.8 cm.

I claim:

1. A new and distinct cultivar of geranium plant named 'Fistaneon', as described and illustrated herein.

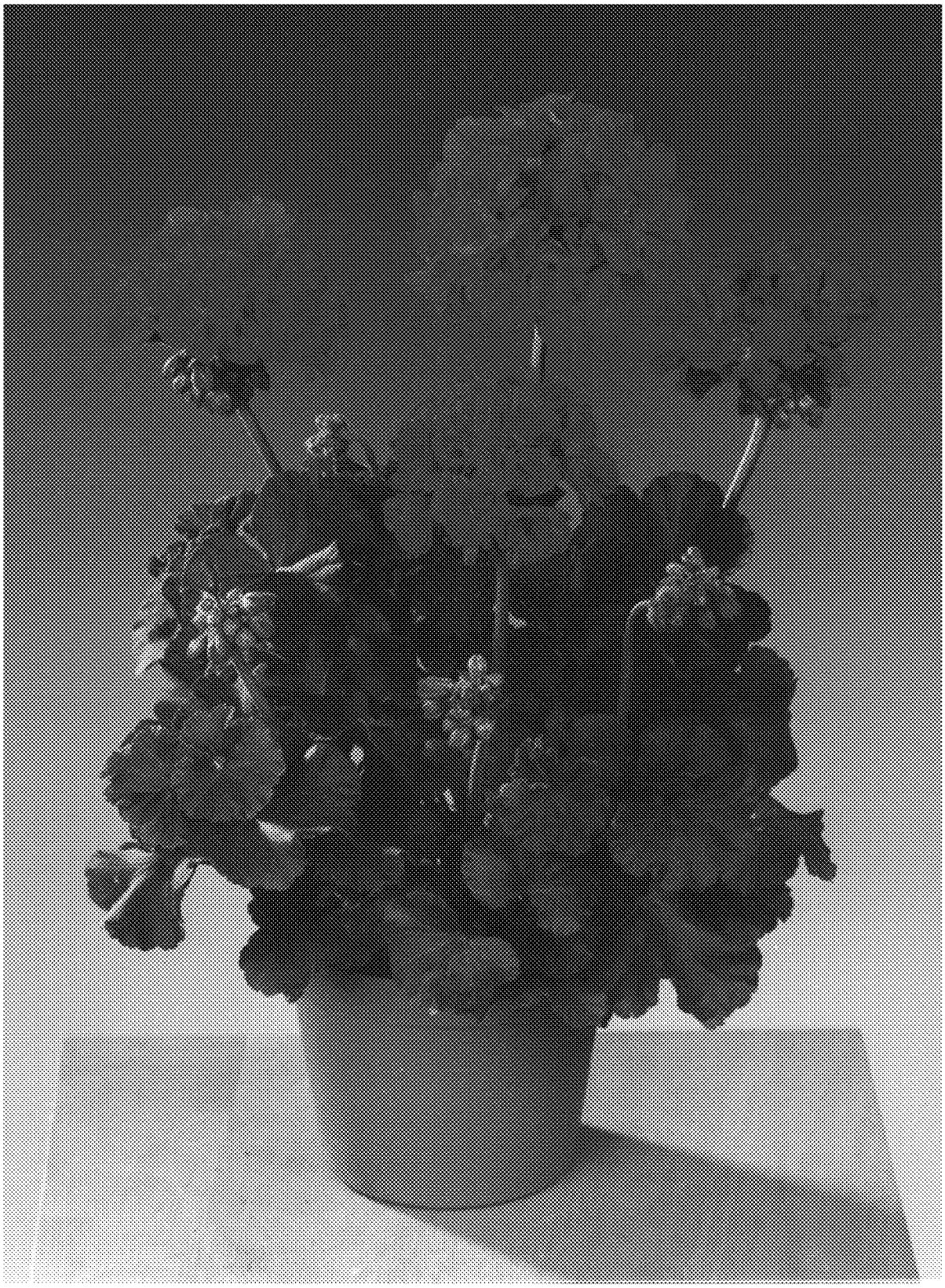

* * * * *